(12) United States Patent
Toyoda

(10) Patent No.: US 9,642,512 B2  
(45) Date of Patent: May 9, 2017

(54) SWITCHING VALVE UNIT AND ENDOSCOPE APPARATUS

(71) Applicant: FUJIFILM Corporation, Tokyo (JP)

(72) Inventor: Yusuke Toyoda, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 296 days.

(21) Appl. No.: 14/608,533

(22) Filed: Jan. 29, 2015

(65) Prior Publication Data
US 2015/0216393 A1   Aug. 6, 2015

(30) Foreign Application Priority Data

Feb. 6, 2014   (JP) .................................. 2014-021780

(51) Int. Cl.
| A61B 1/12 | (2006.01) |
| A61B 1/00 | (2006.01) |
| A61B 1/015 | (2006.01) |

(52) U.S. Cl.
CPC .......... *A61B 1/00068* (2013.01); *A61B 1/015* (2013.01); *A61B 1/00094* (2013.01)

(58) Field of Classification Search
CPC . A61B 1/00068; A61B 1/00094; A61B 1/015; A61B 1/00066; A61B 1/0008; A61B 1/00119; A61B 1/00121; A61B 1/00128
USPC .................................................. 600/157–159
See application file for complete search history.

(56) References Cited

U.S. PATENT DOCUMENTS 5,840,015 A   11/1998   Ogino

FOREIGN PATENT DOCUMENTS

| JP | 8-252216 A | 10/1996 |
| JP | 2004-223121 A | 8/2004 |
| JP | 2006-271890 A | 10/2006 |

OTHER PUBLICATIONS

Extended European Search Report, dated Apr. 21, 2015, for European Patent Application No. 15151696.0.

*Primary Examiner* — Timothy J Neal  
(74) *Attorney, Agent, or Firm* — Birch, Stewart, Kolasch & Birch, LLP

(57) ABSTRACT

A suction button unit for changeover between a suction source and a suction opening includes a piston chamber extending axially. A suction port hole is formed at a lower end of the piston chamber, for connection with the suction opening. An exhaust port hole is formed in a chamber inner wall of the piston chamber, for connection with the suction source. A piston rod is received in the piston chamber, has a first piston end protruding upwards, for shifting from a first position to a second position upon depression. The exhaust port hole is externally opened in case the piston rod is in the first position, but caused to communicate with the suction port hole in case the piston rod is in the second position. A tilting device tilts the piston rod relative to an axial direction of the piston chamber while the piston rod is in the first position.

11 Claims, 14 Drawing Sheets

SWITCHING VALVE UNIT AND ENDOSCOPE APPARATUS

CROSS-REFERENCE TO RELATED APPLICATION

This application claims priority under 35 USC 119 from Japanese Patent Application No. 2014-021780, filed 6 Feb. 2014, the disclosure of which is incorporated by reference herein.

BACKGROUND OF THE INVENTION

1. Field of the Invention

The present invention relates to a switching valve unit and an endoscope apparatus. More particularly, the present invention relates to a switching valve unit and an endoscope apparatus, in which failure in closing in a closed state between plural flow channels can be prevented, and operability of manual depression can be high.

2. Description Related to the Prior Art

An endoscope includes an elongated tube, and a tube channel or suction channel. The elongated tube is entered in a body cavity of a patient, for imaging an object of interest. The tube channel extends through the elongated tube to a suction opening at a distal end. A switching valve unit is disposed on a control handle of the endoscope. The tube channel is coupled to the switching valve unit. The tube channel is an instrument channel and also a suction channel. Namely, the tube channel is used for entry of a medical instrument, such as a forceps. Also, the tube channel is used for suction of fluid. The tube channel may have a structure with branches.

Plural conduits are coupled to the switching valve unit, including an exhaust conduit and the tube channel. The exhaust conduit extends to a suction source, such as a suction pump. The switching valve unit is changeable over by manipulation of depression between a closed state and a flow-through state. In the closed state, the tube channel is closed from communication with the exhaust conduit. In the flow-through state, the tube channel is caused to communicate with the exhaust conduit for enabling suction.

An example of the switching valve unit is a suction button unit, and includes a valve cylinder and a piston rod. The valve cylinder includes a piston chamber, a suction port hole and an exhaust port hole. The piston chamber has open ends. The suction port hole is disposed at a lower end of the piston chamber, and communicates with the tube channel. The exhaust port hole is formed through an inner surface of the piston chamber, and communicates with the exhaust conduit. The piston rod is received in the piston chamber, and is shiftable from a first position to a second position by manipulation of depression. The piston rod includes a side opening, an end opening and a flow path. The side opening becomes aligned with the exhaust port hole in case the piston rod is in the second position. The end opening is formed in a lower end, and communicates with the suction port hole. The flow path is formed to communicate between the side opening and the end opening.

U.S. Pat. No. 5,840,015 (corresponding to JP-A 8-252216) discloses the suction button unit in which seal packing is disposed around the side opening for preventing suction of the atmosphere through a gap space between the piston rod and the valve cylinder with negative pressure of the suction source in the flow-through state. In U.S. Pat. No. 5,840,015 and JP-A 2006-271890, the suction button unit is an O-ring and the like of a ring shape fitted on a lower end of the piston rod. JP-A 2004-223121 (corresponding to DE-B 10 2004 003857) discloses the suction button unit including a button cap, a cap device or cylinder cap, and the seal packing, arranged on the piston rod. The cap device is disposed on the valve cylinder and receives the button cap. The seal packing is so disposed that the cap device receives the button cap in case the piston rod is depressed for the flow-through state. The seal packing seals a gap space between the button cap and the cap device.

However, the seal packing of U.S. Pat. No. 5,840,015 and JP-A 2006-271890 has a problem of degradation. Response to manipulation of the depression to the piston rod may become poor, or return of the piston rod after interrupting the depression may be too slow, due to the degradation of the seal packing with time between the piston rod and the valve cylinder in the suction button unit. Furthermore, air of the atmosphere is likely to be drawn through a weakened portion of the seal packing by the suction in the suction button unit of U.S. Pat. No. 5,840,015 and JP-A 2006-271890. In JP-A 2004-223121, there is no suggestion of seal packing between the piston rod and the valve cylinder in the suction button unit. While the piston rod is in the first position for the closed state, negative pressure occurs in the tube channel through the flow path due to a fine gap space between an outer surface of the piston rod and an inner surface of the valve cylinder. Unwanted suction is likely to occur at the distal opening of the tube channel.

SUMMARY OF THE INVENTION

In view of the foregoing problems, an object of the present invention is to provide a switching valve unit and an endoscope apparatus, in which failure in closing in a closed state between plural flow channels can be prevented, and operability of manual depression can be high.

In order to achieve the above and other objects and advantages of this invention, a switching valve unit for an endoscope apparatus, for changeover in a conduit extending between a suction source and a suction opening, is provided. A valve cylinder is mounted on a control handle of the endoscope apparatus, has a piston chamber. A cylinder opening is formed at an upper end of the piston chamber. A suction port hole is formed at a lower end of the piston chamber, and adapted to connection with the suction opening. An exhaust port hole is formed in a chamber inner wall of the piston chamber, and adapted to connection with the suction source. A piston rod is received in the piston chamber, has a first piston end protruding from the cylinder opening, for shifting from a first position to a second position upon depression. A side opening is formed in a peripheral side wall of the piston rod, aligned with the exhaust port hole in case the piston rod is in the second position, and closed by the chamber inner wall of the piston chamber in case the piston rod is in the first position. An end opening is formed at a second piston end of the piston rod, for alignment with the suction port hole. A first flow path is formed in the piston rod between the side opening and the end opening, for communication of the exhaust port hole to the suction port hole in case the piston rod is in the second position. A peripheral groove is formed in the peripheral side wall of the piston rod, aligned with the exhaust port hole in case the piston rod is in the first position, and closed by the chamber inner wall of the piston chamber in case the piston rod is in the second position. A flow path surface is formed with the peripheral side wall of the piston rod to extend from the peripheral groove to the first piston end of the piston rod. A second flow path is constituted by the peripheral groove and the flow path surface, for externally opening the exhaust port hole in case the piston rod is in the first position. An anti-rotation device prevents the piston rod from rotating relative to the piston chamber. A tilting device tilts the piston rod relative to an axial direction of the valve cylinder while the piston rod is in the first position.

Preferably, furthermore, a cap device is disposed on the valve cylinder, for keeping the piston rod positioned in the cylinder opening of the piston chamber. A button cap is mounted on the first piston end. A bias device is disposed between the button cap and the cap device, for biasing the piston rod to the first position, to press the piston rod to the cap device. The button cap moves the piston rod to the second position and contacts the cap device upon being depressed against the bias device.

Preferably, the tilting device includes a projection, formed with a first part selected from the piston rod and the cap device, to protrude toward a second part selected from the piston rod and the cap device, for contacting the second part in case the piston rod is in the first position.

In another preferred embodiment, the tilting device includes an inclined surface, formed with a first part selected from the piston rod and the cap device, for contacting a second part selected from the piston rod and the cap device in case the piston rod is in the first position.

Preferably, the cap device supports the piston rod and the bias device, and is removable from the valve cylinder.

Preferably, the tilting device tilts the piston rod in a direction toward the side opening relative to the valve cylinder, for tightening closing of the side opening with the chamber inner wall.

Preferably, furthermore, a removal facilitator is disposed at the end opening, for facilitating suction of residue remaining in the end opening.

Preferably, the removal facilitator includes a tapered surface, formed in the end opening, and inclined for increasing a diameter toward the second piston end.

In another preferred embodiment, the removal facilitator is an inner shoulder at which an inner diameter of the end opening is larger than an inner diameter of the first flow path.

In still another preferred embodiment, the removal facilitator includes a discharge hole, disposed near to the end opening, and formed through the peripheral side wall of the piston rod from the first flow path.

Also, an endoscope apparatus is provided, and includes an elongated tube for entry in a body cavity. A control handle is disposed at a proximal end of the elongated tube. An exhaust conduit is disposed to extend from the control handle, for connection to a suction source. A suction conduit is formed through the elongated tube, has a suction opening at a distal end thereof. A valve cylinder is mounted on the control handle, has a piston chamber. A cylinder opening is formed at an upper end of the piston chamber. A suction port hole is formed at a lower end of the piston chamber, and coupled with the suction conduit. An exhaust port hole is formed in a chamber inner wall of the piston chamber, and coupled with the exhaust conduit. A piston rod is received in the piston chamber, has a first piston end protruding from the cylinder opening, for shifting from a first position to a second position upon depression. A side opening is formed in a peripheral side wall of the piston rod, aligned with the exhaust port hole in case the piston rod is in the second position, and closed by the chamber inner wall of the piston chamber in case the piston rod is in the first position. An end opening is formed at a second piston end of the piston rod, for alignment with the suction port hole. A first flow path is formed in the piston rod between the side opening and the end opening, for communication of the exhaust port hole to the suction port hole in case the piston rod is in the second position. A peripheral groove is formed in the peripheral side wall of the piston rod, aligned with the exhaust port hole in case the piston rod is in the first position, and closed by the chamber inner wall of the piston chamber in case the piston rod is in the second position. A flow path surface is formed with the peripheral side wall of the piston rod to extend from the peripheral groove to the first piston end of the piston rod. A second flow path is constituted by the peripheral groove and the flow path surface, for externally opening the exhaust port hole in case the piston rod is in the first position. An anti-rotation device prevents the piston rod from rotating relative to the piston chamber. A tilting device tilts the piston rod relative to an axial direction of the valve cylinder while the piston rod is in the first position.

Consequently, failure in closing in a closed state between plural flow channels can be prevented, because the piston rod can be tilted for tightening the closed state of the piston chamber.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1:
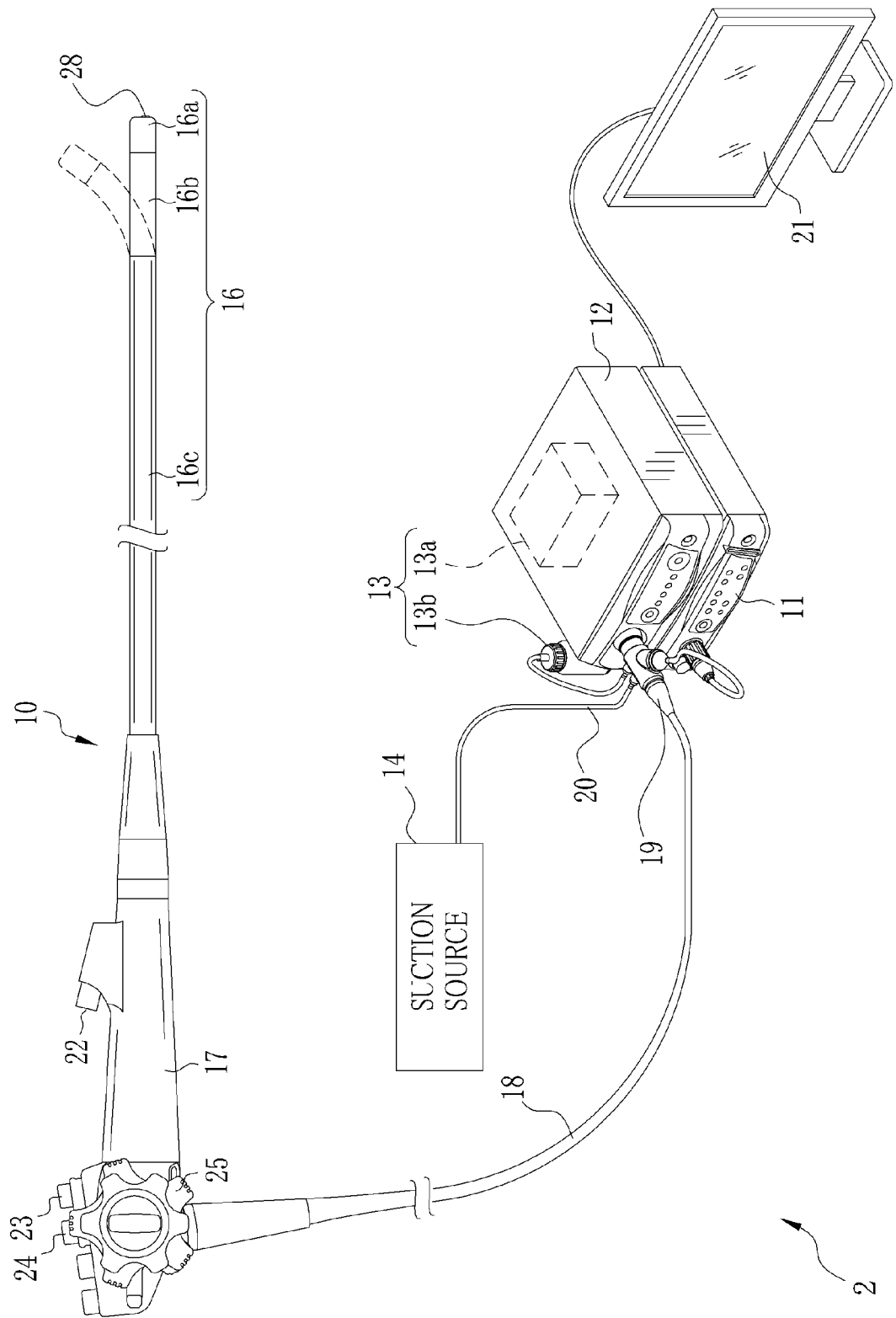
FIG. 1 is an explanatory view illustrating an endoscope system.

In FIG. 1, an endoscope system 2 includes an electronic endoscope apparatus 10, a processing apparatus 11, a light source apparatus 12, a fluid supply source 13, and a suction source 14 or suction apparatus. The fluid supply source 13 includes an air pump 13a as air supply source, and a water tank 13b as water supply source. The air pump 13a is a known device incorporated in the light source apparatus 12, for supplying air. The water tank 13b is disposed outside the light source apparatus 12, and stores washing water. The endoscope apparatus 10 includes an elongated tube 16 or guide tube, a control handle 17 and a universal cable 18. The elongated tube 16 is entered in a body cavity. The control handle 17 is disposed at a proximal end of the elongated tube 16. The universal cable 18 operates for connection to the processing apparatus 11 and the light source apparatus 12.

Figure 2:
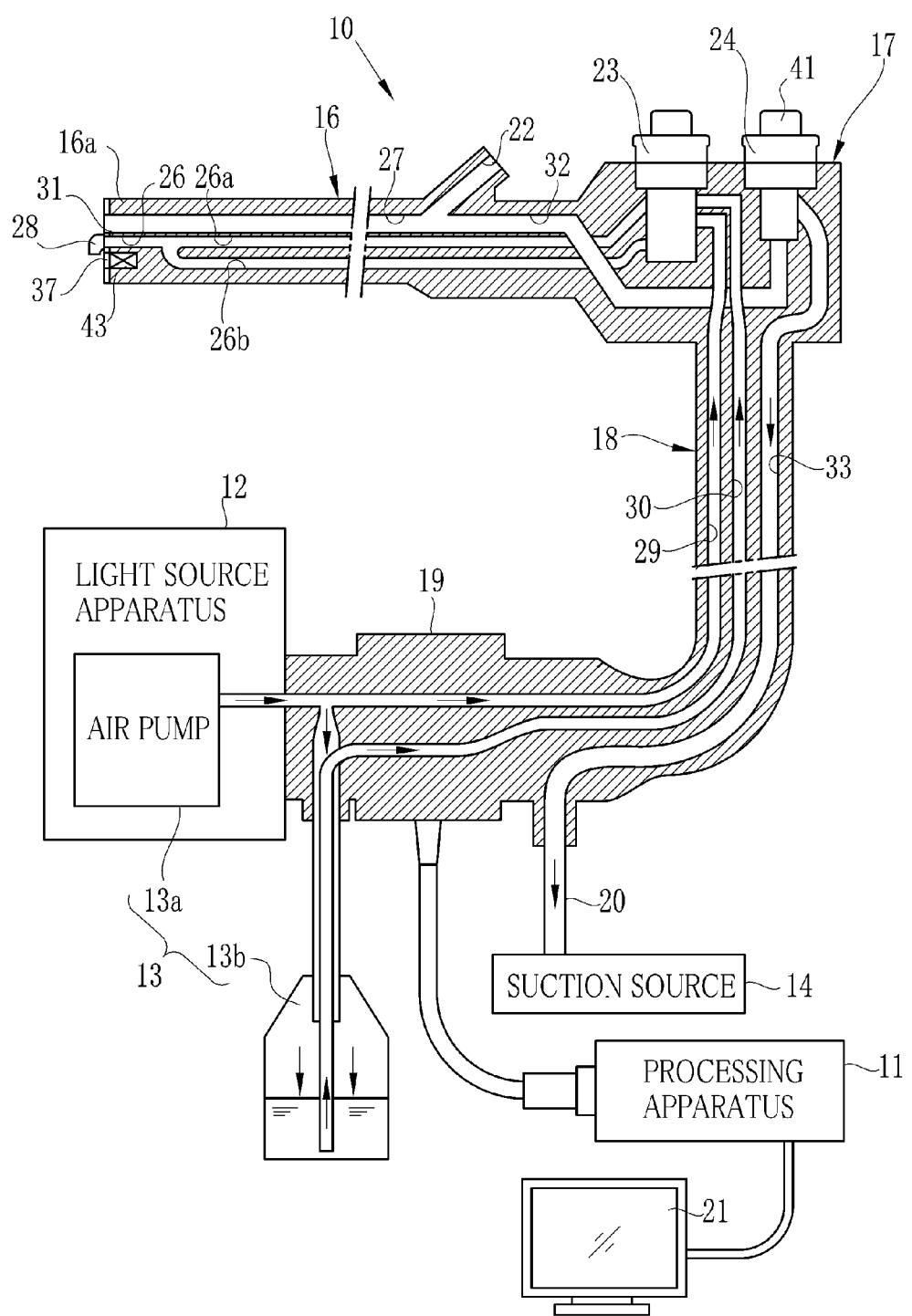
FIG. 2 is an explanatory view in a section illustrating an endoscope apparatus.

The elongated tube 16 has a tip device 16a, a steering device 16b and a flexible tube device 16c. A camera unit 43 or imaging unit of FIG. 2 is incorporated in the tip device 16a for imaging in the body cavity. The steering device 16b at a proximal end of the tip device 16a is bendable for steering. The flexible tube device 16c at a proximal end of the steering device 16b is flexible.

A connector plug 19 is disposed at a proximal end of the universal cable 18. The connector plug 19 is a composite type of connector for connection to the processing apparatus 11, the light source apparatus 12 and the fluid supply source 13. A connection tube 20 couples the connector plug 19 to the suction source 14.

The processing apparatus 11 is electrically connected with the light source apparatus 12. Various elements in the endoscope system 2 are controlled by the processing apparatus 11. A connection cable is disposed through the universal cable 18 and the elongated tube 16. By use of the connection cable, the processing apparatus 11 supplies the endoscope apparatus 10 with power, and controls the camera unit 43. Also, the processing apparatus 11 receives an image signal output by the camera unit 43 through the cable, processes the image signal in the image processing, and generates image data. A monitor display panel 21 in connection with the processing apparatus 11 is driven to display an image of the image data produced by the processing apparatus 11.

The control handle 17 includes a proximal channel opening 22, a fluid button unit 23, a suction button unit 24 or switching valve unit, and steering wheels 25. Rotation of the steering wheels 25 moves wires through the elongated tube 16 back and forth, to bend the steering device 16b up and down and to the right and left. The tip device 16a is directed in a desired direction in the body cavity.

In FIG. 2, a fluid channel 26 and a tube channel 27 or instrument channel are disposed to extend through the elongated tube 16 and the control handle 17. A fluid nozzle 28 is disposed in the tip device 16a, and constitutes a distal end of the fluid channel 26. Two branches are provided at a proximal end of the fluid channel 26, and include an air conduit 26a and a water conduit 26b. The fluid button unit 23 in the control handle 17 is coupled with the air conduit 26a and the water conduit 26b.

An air supply conduit 29 and a water supply conduit 30 are disposed to extend to the fluid button unit 23 in addition to the air conduit 26a and the water conduit 26b. The air supply conduit 29 is coupled with the air pump 13a. The water supply conduit 30 is coupled with the water tank 13b. The air pump 13a supplies air for the purpose of imaging with the endoscope apparatus 10. Note that the gas for supply may be different from air, for example, carbon dioxide gas.

In case the fluid button unit 23 is operated for air supply, air from the air pump 13a is supplied to the fluid nozzle 28. In case the fluid button unit 23 is operated for water supply, water from the water tank 13b is supplied to the fluid nozzle 28 in a condition with the pressure of the air from the air pump 13a. The fluid nozzle 28 selectively ejects the water and air from the fluid channel 26, to wash a viewing window 37.

A suction opening 31 or distal channel opening is disposed at a distal end of the tube channel 27. A proximal end of the tube channel 27 is connected to the proximal channel opening 22.

A medical instrument, such as an injection needle, high frequency knife and the like, are entered into the proximal channel opening 22. A closing device (not shown) closes the proximal channel opening 22 before or after the use of the medical instrument. A suction conduit 32 is a branch of the tube channel 27, and is coupled to the suction button unit 24.

A suction tube 38 having the suction conduit 32 is connected to the suction button unit 24. Also, an exhaust tube 39 or suction source tube is connected to the suction button unit 24. An exhaust conduit 33 or suction source conduit extends through the exhaust tube 39. See FIG. 3. The suction source 14 includes a suction pump or the like as a negative pressure source, and is always active in the course of imaging with the endoscope apparatus 10. In case the suction button unit 24 is depressed for a flow-through state, negative pressure is generated by the suction source 14 for the suction. In case the suction button unit 24 is free for a closed state without depression, the suction is stopped by interrupting application of the negative pressure.

There is a button cap 41 in the suction button unit 24. While the button cap 41 is inactive without being depressed, the exhaust conduit 33 in the exhaust tube 39 (See FIG. 3) is set open to the atmosphere. As the suction source 14 is always active, increase in the load to the suction source 14 must be prevented by opening the exhaust conduit 33 to the atmosphere.

Figure 3:
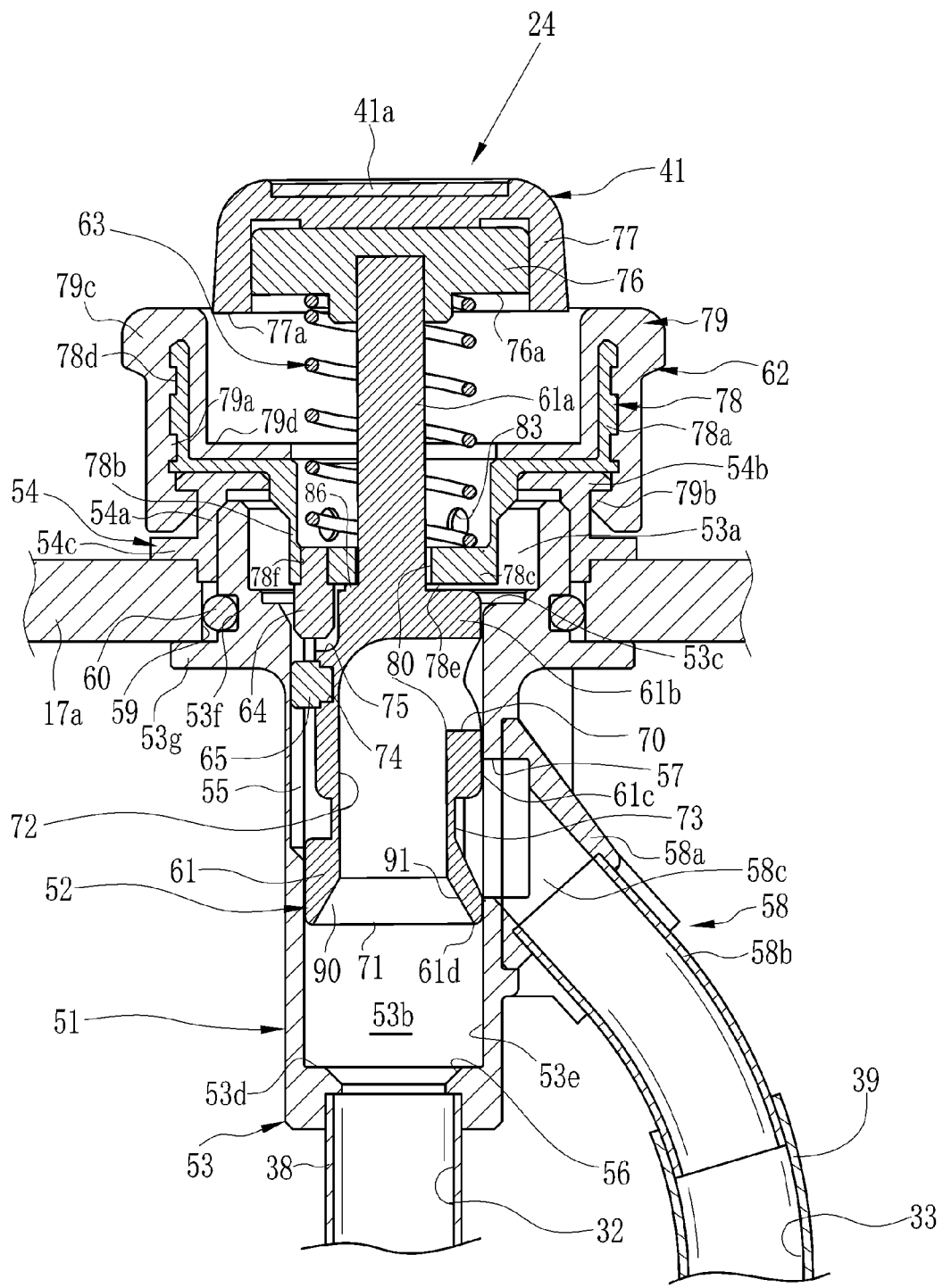
FIG. 3 is a vertical section illustrating a suction button unit.
Figure 10:
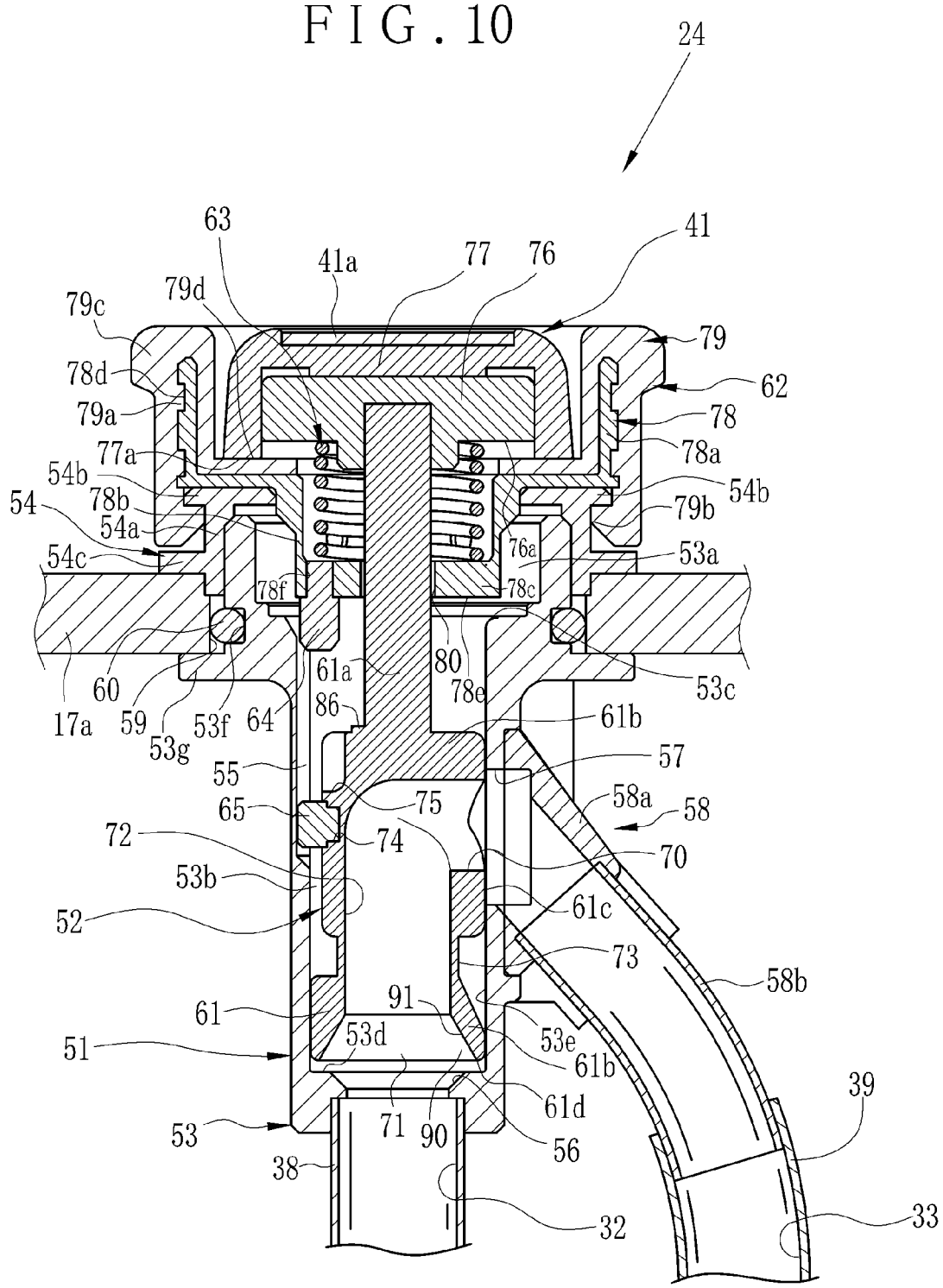
FIG. 10 is a vertical section illustrating the suction button unit in a flow-through state.

Upon depression of the button cap 41, the suction button unit 24 causes the suction conduit 32 of the suction tube 38 of FIGS. 3 and 10 to communicate with the exhaust conduit 33. Force of the suction with the negative pressure increases in the suction conduit 32 and the tube channel 27, to suck fluid through the suction opening 31.

Figure 4:
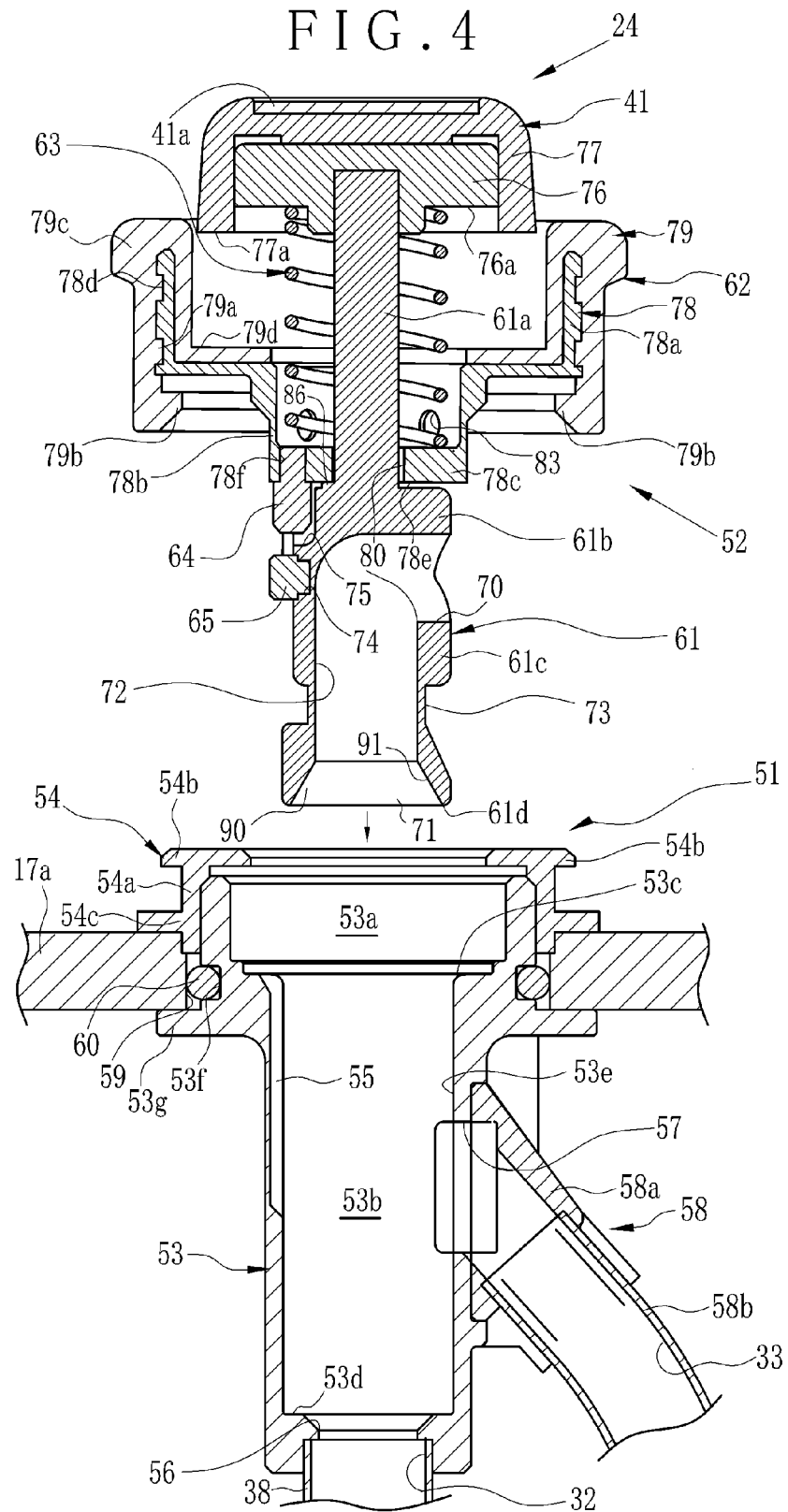
FIG. 4 is a vertical section illustrating the suction button unit of which a piston rod is removed.

In FIG. 4, the suction button unit 24 includes a cylinder device 51 and a piston mechanism 52 mounted in the cylinder device 51 in a removable manner.

The cylinder device 51 includes a valve cylinder 53 and a support ring 54. The valve cylinder 53 is a part of metal. The valve cylinder 53 includes a receiving hole 53a and a piston chamber 53b or valve chamber. The piston chamber 53b is formed axially to extend from the upper end to the lower end.

A cylinder opening 53c (center opening) is an upper end of the piston chamber 53b. An end wall 53d is disposed in the piston chamber 53b at its lower end. A suction port hole 56 is formed in the end wall 53d. The suction conduit 32 is coupled to the suction port hole 56. A chamber inner wall 53e is provided in the piston chamber 53b. An exhaust port hole 57 or suction source port hole is formed in the chamber inner wall 53e. A conduit coupling 58 for suction couples the exhaust conduit 33 to the exhaust port hole 57. The conduit coupling 58 includes a coupling port 58a and a coupling sleeve 58b. The coupling port 58a is a portion of the valve cylinder 53. The coupling sleeve 58b is fixedly coupled to the coupling port 58a and the exhaust tube 39. The exhaust conduit 33 extends through the coupling sleeve 58b. An exhaust flow path 58c or suction source flow path extends through the coupling port 58a. A male thread (not shown), a peripheral groove 53f and a support flange 53g are formed with the periphery of the valve cylinder 53. A female thread (not shown) of the support ring 54 is engaged helically with the male thread. A handle housing 17a of the control handle 17 contacts the support flange 53g. Amount opening 59 is formed through the handle housing 17a, and receives upward entry of the valve cylinder 53.

A key groove 55 (second anti-rotation groove) in an anti-rotation device is formed with the piston chamber 53b. The key groove 55 extends to the upper end of the valve cylinder 53, and is formed in the chamber inner wall 53e partially in the axial direction in correspondence with the exhaust port hole 57. A piston rod 61 or valve stem is prevented from rotating by use of the key groove 55.

The support ring 54 includes a ring wall 54a, a coupling flange 54b and a support flange 54c. The coupling flange 54b is formed around the ring wall 54a. The support flange 54c is formed around the ring wall 54a and disposed lower than the coupling flange 54b. A female thread (not shown) is formed on an inner surface of the ring wall 54a. The female thread is disposed at a lower end of the inner surface, and becomes helically engaged with the male thread of the valve cylinder 53. The support flanges 54c and 53g squeeze a portion of the handle housing 17a around the mount opening 59, to mount the valve cylinder 53 on the handle housing 17a. An O-ring 60 is fitted in the peripheral groove 53f, and seals clearance between the handle housing 17a and the valve cylinder 53 in a fluid-tight manner.

The piston mechanism 52 includes the piston rod 61, a cap device 62 or cylinder cap, the button cap 41, a compression coil spring 63 (bias device), a first anti-rotation projection 64 (key projection), and a key projection 65 (second anti-rotation projection) in an anti-rotation device. The piston rod 61 includes an end shaft 61a (piston head) at an upper end, and a valve shaft 61b or piston shaft at a lower end. The end shaft 61a has a smaller diameter than the valve shaft 61b.

Figure 5:
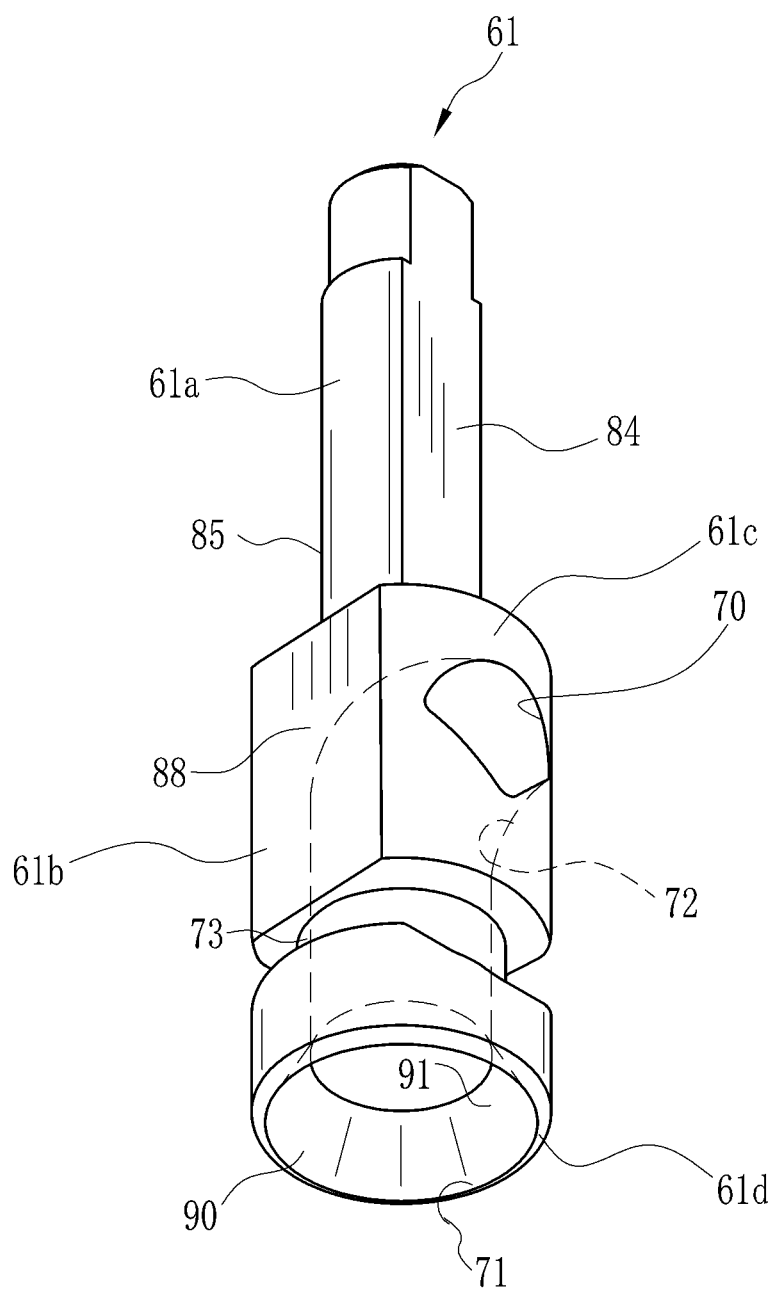
FIG. 5 is a perspective view illustrating a piston rod.
Figure 6:
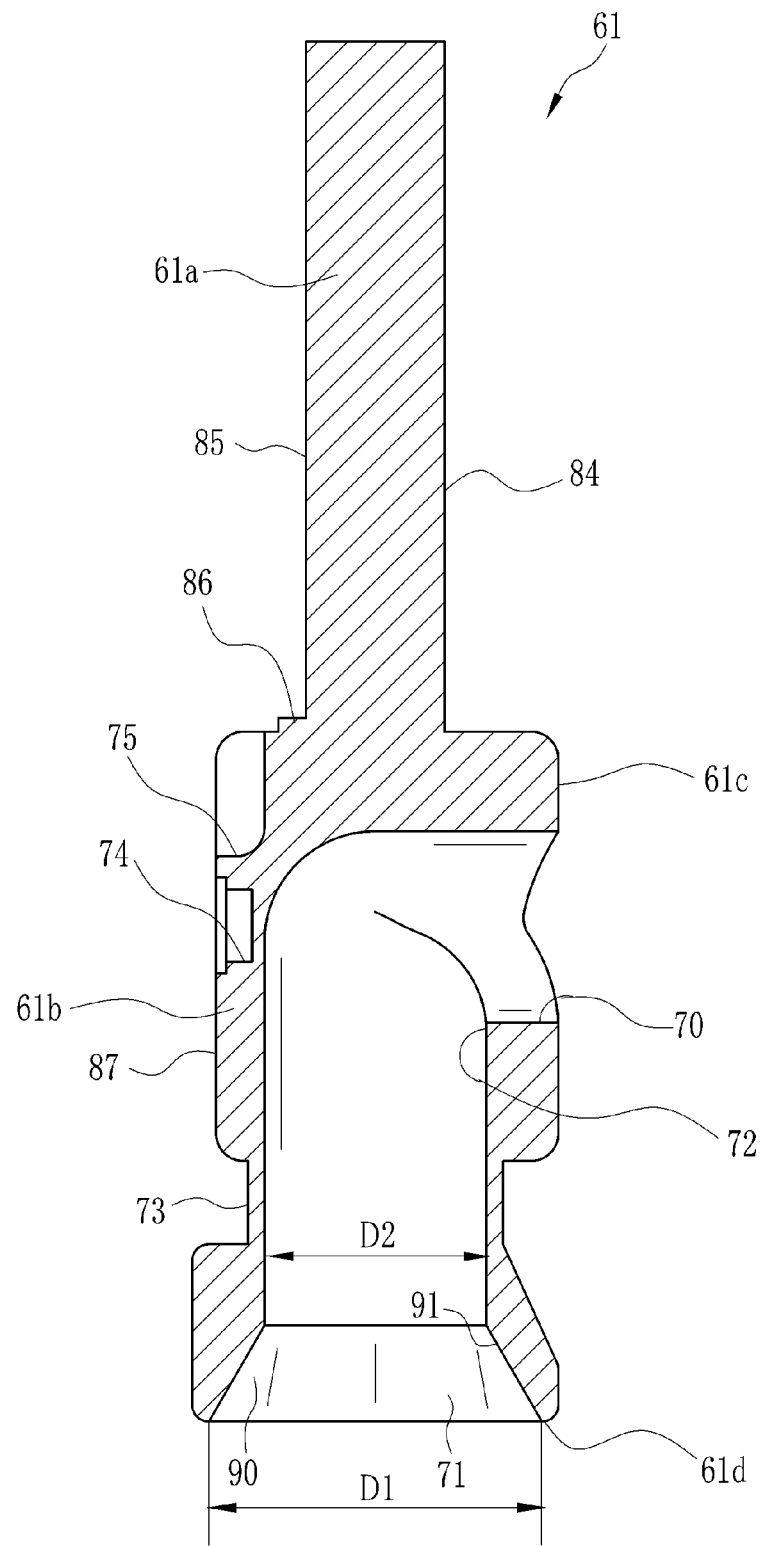
FIG. 6 is a vertical section illustrating the piston rod.

In FIG. 5, the valve shaft 61b has a peripheral side wall 61c, a side opening 70, an end opening 71 and a first flow path 72. The side opening 70 is formed through the peripheral side wall 61c. The end opening 71 is open in a lower piston end 61d (second piston end). The first flow path 72 is a through hole in an L-shape to extend between the side opening 70 and the end opening 71. A peripheral groove 73 is formed in the peripheral side wall 61c of the valve shaft 61b. In FIG. 6, a first anti-rotation groove 75 (key groove) is formed in the peripheral side wall 61c and opposite to the side opening 70. Amount hole 74 is disposed lower than the first anti-rotation groove 75. The first anti-rotation groove 75 extends from the upper end downwards in parallel with the axial direction. While the piston rod 61 is in a first position, the side opening 70 is opposed to the chamber inner wall 53e of the piston chamber 53b. In case the piston rod 61 is in a second position, the side opening 70 is aligned with the exhaust port hole 57.

Figure 7:
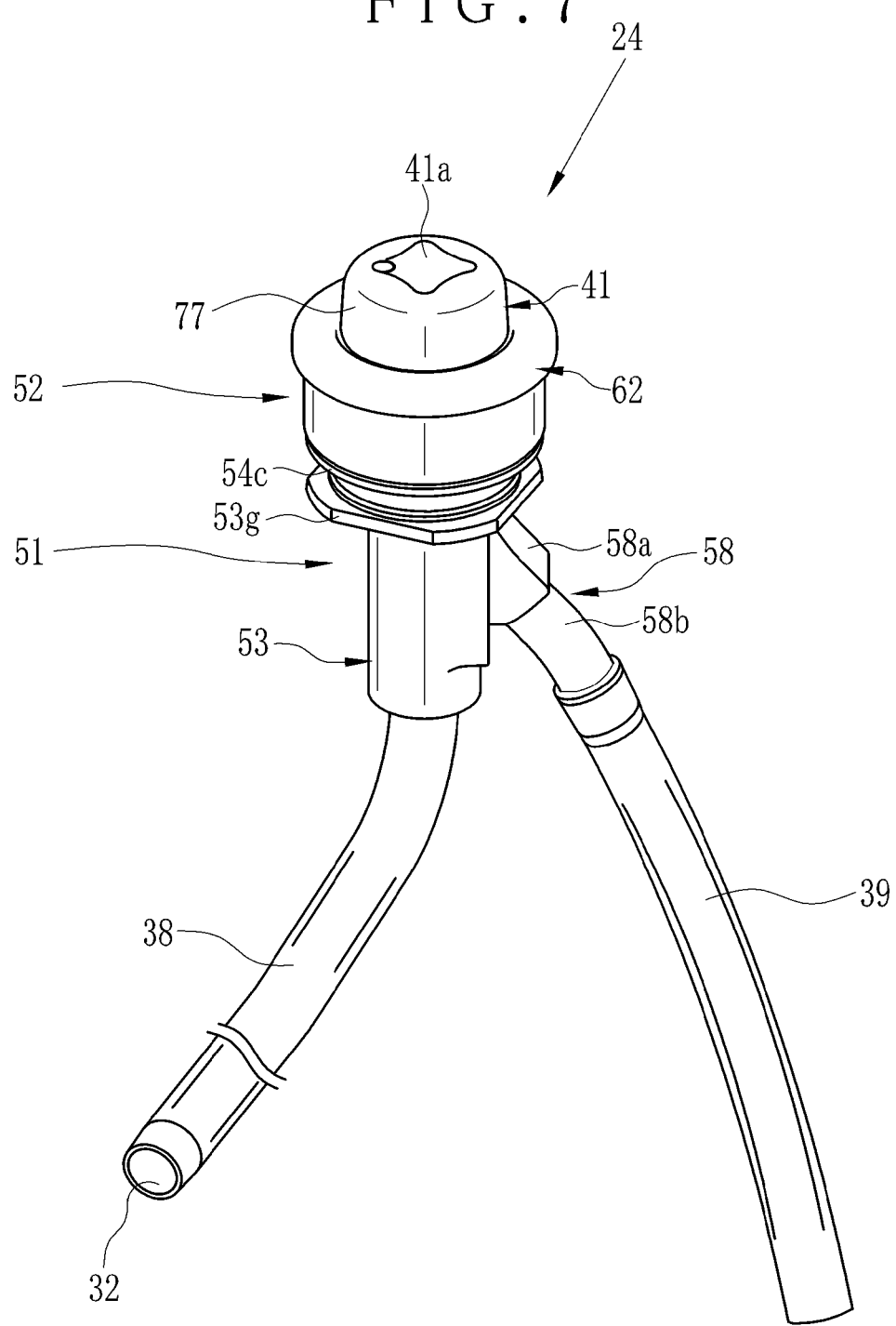
FIG. 7 is a perspective view illustrating the suction button unit.

In FIG. 4, the button cap 41 is attached to the end of the end shaft 61a fixedly. The button cap 41 includes a button mount 76 of metal, and a button head 77 of resin for covering the button mount 76. In FIG. 7, a button indicia 41a is formed on the button head 77. The button indicia 41a indicates a portion of depression at the time of manipulation of a user.

The cap device 62 and the compression coil spring 63 a are disposed between the button cap 41 alnd the valve shaft 61b. The end shaft 61a is disposed to extend into the cap device 62 and the compression coil spring 63. The cap device 62 includes an intermediate sleeve 78 of metal, and a cover sleeve 79. The intermediate sleeve 78 includes an upper sleeve portion 78a and a lower sleeve portion 78b. A lower plate 78c of the lower sleeve portion 78b has an axial hole 80. The end shaft 61a extends through the axial hole 80. Plural vents 83 are formed in the lower sleeve portion 78b, and open to the atmosphere.

The cover sleeve 79 is formed from rubber or resin, and fitted on the upper sleeve portion 78a. A coupling recess 78d is formed in the outer surface of the upper sleeve portion 78a. A coupling projection 79a is formed on the cover sleeve 79 and engaged with the coupling recess 78d. The cover sleeve 79 is kept positioned on the upper sleeve portion 78a without drop by the engagement between the coupling recess 78d and the coupling projection 79a. The cover sleeve 79 has a shape with a lower plate and is fitted on inner and outer surfaces of the upper sleeve portion 78a.

Latch projections 79b are formed to project from a lower end of the cover sleeve 79. The latch projections 79b, in the course of combining the piston mechanism 52 with the cylinder device 51, are moved to pass the coupling flange 54b, and become retained on the coupling flange 54b. In FIG. 3, the piston mechanism 52 can be reliably mounted in the cylinder device 51. To remove the piston mechanism 52 from the cylinder device 51, an outer flange 79c of the cap device 62 is grasped manually by fingers of a user, to move up the piston mechanism 52. Thus, the latch projections 79b are disengaged from the coupling flange 54b.

The suction conduit 32, the exhaust conduit 33, the piston chamber 53b and the like are contaminated with body fluid or other contaminating fluid after the use of the endoscope apparatus 10 for imaging. Those elements must be washed carefully by use of a brush or the like to remove the fluid. To this end, the latch projections 79b are disengaged from the coupling flange 54b. In FIG. 4, the piston mechanism 52 is removed from the cylinder device 51, so that the suction conduit 32, the exhaust conduit 33 and the piston chamber 53b become accessible through the cylinder opening 53c and can be cleaned up easily. Note that the piston mechanism 52 after use is washed and reused. Otherwise, the piston mechanism 52 being used may be discarded before a new piston mechanism 52 is mounted for updating.

The compression coil spring 63 has upper and lower spring ends. The upper end is mounted on a plate surface 76a of the button mount 76. The lower end is mounted on the lower plate 78c of the lower sleeve portion 78b. The button cap 41 is always biased by the compression coil spring 63 upwards inside the cap device 62. The lower plate 78c has a lower end surface 78e as a second end surface of the cap device 62. The end of the valve shaft 61b contacts the lower end surface 78e.

Figure 9:
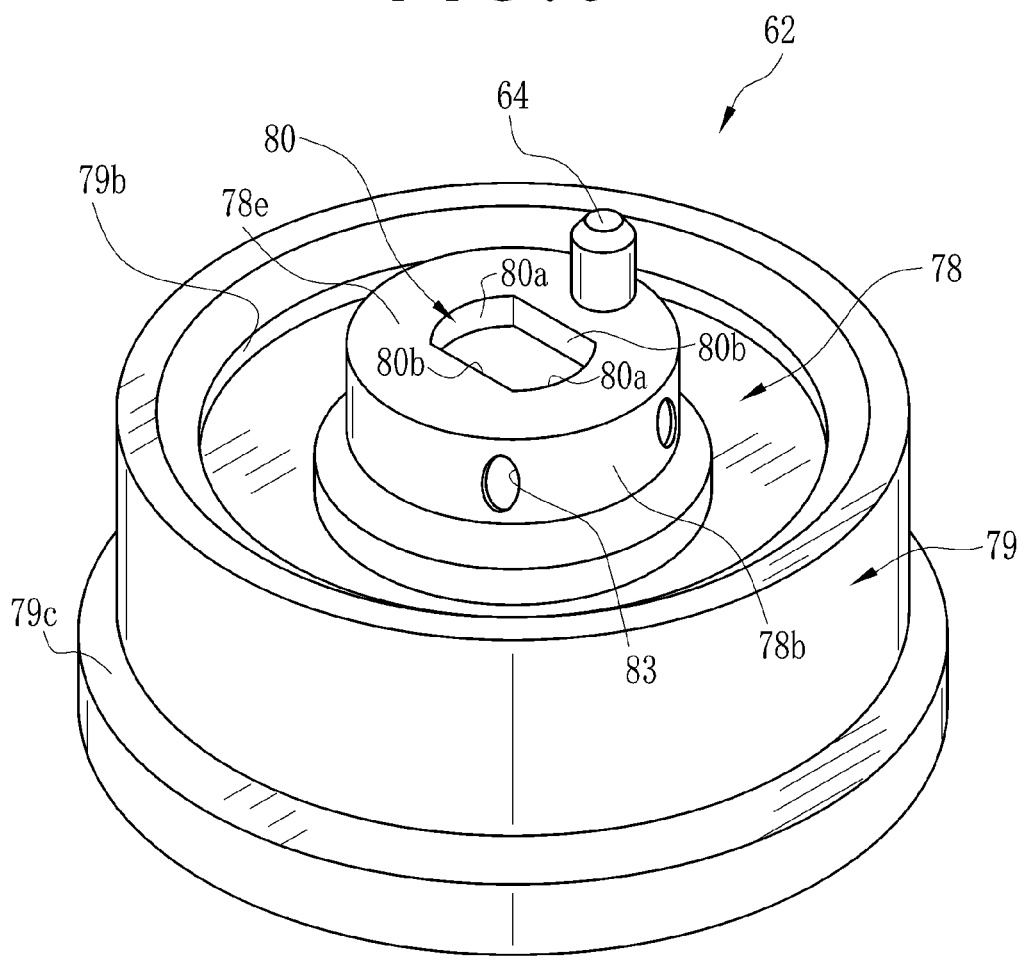
FIG. 9 is a bottom perspective view illustrating a cap device.

A mount hole 78f is formed in the lower plate 78c and extends in parallel with the axis of the valve cylinder 53. An upper end of the first anti-rotation projection 64 is fixedly fitted in the mount hole 78f. In FIG. 9, the first anti-rotation projection 64 protrudes from the lower end surface 78e and contained in the first anti-rotation groove 75 of the valve shaft 61b. The piston rod 61 is kept from rotating relative to the cap device 62 by engagement of the first anti-rotation projection 64 with the first anti-rotation groove 75.

In FIG. 4, a pin for the key projection 65 is fixedly attached to the mount hole 74 of the piston rod 61. The key projection 65 and the key groove 55 in the valve cylinder 53 perform anti-rotation operation between the valve cylinder 53 and the piston rod 61. The key projection 65 is received in the key groove 55 to prevent the relative rotation between the valve cylinder 53 and the piston rod 61.

Figure 8:
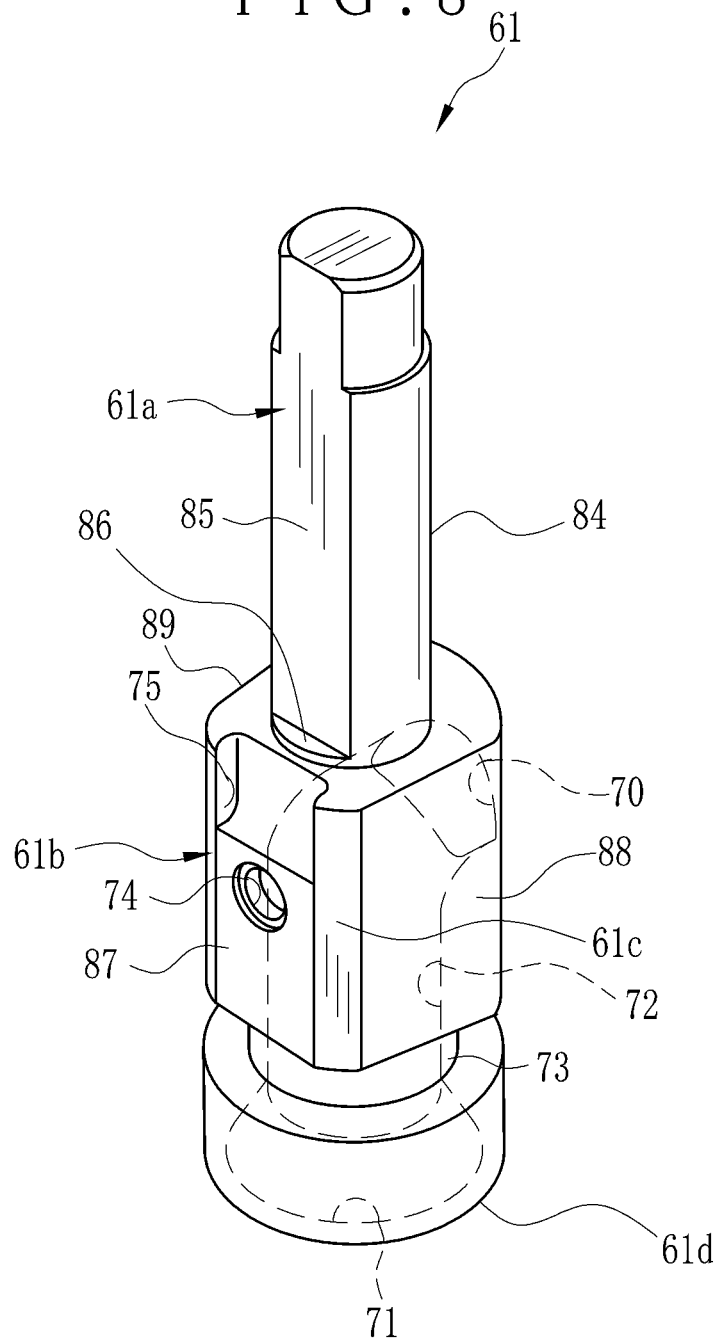
FIG. 8 is a perspective view illustrating the piston rod.

In FIG. 8, the end shaft 61a includes receiving surfaces 84 and 85, and a shoulder projection 86 as a tilting device. The receiving surfaces 84 and 85 are formed by chamfering a cylindrical shape of the end shaft 61a, and extend in parallel with one another. The shoulder projection 86 is formed at a lower end of the receiving surface 85. The receiving surface 84 extends to the upper end of the valve shaft 61b. The receiving surface 85 extends to the shoulder projection 86 disposed with the valve shaft 61*b*. The shoulder projection 86 projects from the upper end of the valve shaft 61*b* and with the outer surface of the end shaft 61*a*. In relation to a radial direction of the piston rod 61, the shoulder projection 86 is positioned in reverse to the side opening 70. As the receiving surface 84 extends to the upper end of the valve shaft 61*b*, the portion of the shoulder projection 86 at the upper end of the valve shaft 61*b* is positioned high under the end shaft 61*a*. The shoulder projection 86 operates as a tilting device for tilting the piston rod 61 by contacting the cap device 62.

In FIG. 9, the axial hole 80 in the cap device 62 for receiving the end shaft 61*a* (See FIG. 4) has two arcuate surfaces 80*a* and two flat surfaces 80*b* for engagement. An inner diameter of the arcuate surfaces 80*a* of the axial hole 80 is larger than an outer diameter of the end shaft 61*a*, and smaller than an outer diameter of the valve shaft 61*b*. An interval between the flat surfaces 80*b* is larger than that between the receiving surfaces 84 and 85, and smaller than the outer diameter of the end shaft 61*a*. It is possible to prevent the piston rod 61 from rotating relative to the cap device 62 and prevent dropping of the piston rod 61 from the valve cylinder 53, owing to the engagement of the flat surfaces 80*b* with the receiving surfaces 84 and 85.

The piston rod 61 is positioned by the cap device 62, and shifts between the first position of FIG. 3 and the second position of FIG. 10. The first position is an inactive position of the button cap 41 without depression, so that the button cap 41 is the farthest from the cylinder opening 53*c*. The piston rod 61 is biased by the compression coil spring 63 toward the upper end of the valve cylinder 53 with the button cap 41, to set the shoulder projection 86 in contact with the lower end surface 78*e* stably. Then the piston rod 61 is in the first position. The second position is an active position of the button cap 41 upon the depression. The button cap 41 is the nearest to the cylinder opening 53*c* and prevented from further depression. While the button cap 41 is depressed, the piston rod 61 moves downwards in the valve cylinder 53 against the bias of the compression coil spring 63. The button cap 41 becomes contained in the cap device 62. An end surface 77*a* of the button head 77 comes in contact with an inner surface 79*d* of the cover sleeve 79 and becomes stopped. The piston rod 61 comes to the second position.

At the time of the first position, the peripheral groove 73 is aligned with the exhaust port hole 57 . The peripheral groove 73 is formed circumferentially in the valve shaft 61*b*. Three flow path surfaces 87, 88 and 89 or flow path recesses of FIG. 8 are formed with the peripheral side wall 61*c* of the valve shaft 61*b* and from the peripheral groove 73 to the upper end of the valve shaft 61*b*, and arranged rectangularly with 90 degrees, to communicate with the peripheral groove 73. The flow path surfaces 87-89 are formed by chamfering the cylindrical surface of the piston rod 61. Incase the piston rod 61 is in the first position, a second flow path, which is constituted by the peripheral groove 73 and the flow path surfaces 87-89, causes the exhaust port hole 57 to open to the atmosphere through the peripheral groove 73, the flow path surfaces 87-89, the space in the support ring 54, and the vents 83. Thus, the suction source 14 draws air from the atmosphere. Note that the peripheral groove 73 may not be formed circumferentially around the valve shaft 61*b*. The peripheral groove 73 can be formed only partially in the circumferential direction for the purpose of communicating with the exhaust port hole 57 and with the flow path surfaces 87-89 at the time of the first position.

While the piston rod 61 is in the second position, the side opening 70 is positioned at the exhaust port hole 57 as illustrated in FIG. 10. As the first flow path 72 is formed in the piston rod 61 for communication of the side opening 70 to the end opening 71, the suction source 14 performs the suction from the suction conduit 32. Thus, fluid can be removed through the suction opening 31 in the tip device 16*a*.

Figure 11A:
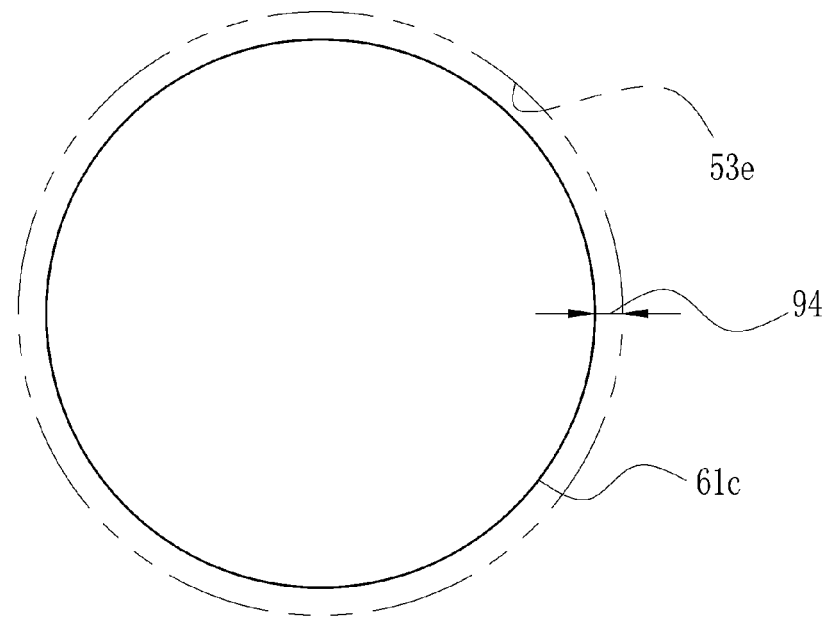
FIG. 11A is a plan illustrating a state of the piston rod extending in a properly vertical direction.
Figure 11B:
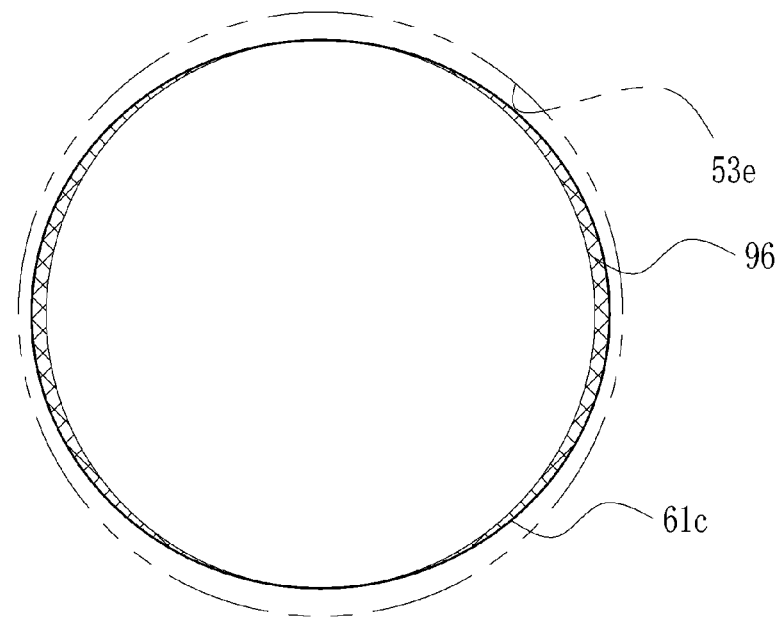
FIG. 11B is a plan illustrating a tilted state of the piston rod.

In the present construction, the shoulder projection 86 contacts the lower end surface 78*e* of the cap device 62, to tilt the piston rod 61 in the first position. The tilt is within a range of a small gap space 94 between the chamber inner wall 53*e* of the piston chamber 53*b* and the peripheral side wall 61*c* of the valve shaft 61*b*. In FIG. 11A, shapes of cross sections of the chamber inner wall 53*e* of the piston chamber 53*b* and the peripheral side wall 61*c* of the valve shaft 61*b* are circular. In FIG. 11B, the shape of the cross section of the peripheral side wall 61*c* of the valve shaft 61*b* become elliptic upon the small tilt of the piston rod 61. Thus, an area of the gap space 94 decreases by an amount of a hatched area 96 according to the elliptic form of the cross section of the piston rod 61, as the circular shape of the cross section of the chamber inner wall 53*e* of the piston chamber 53*b* is unchanged. Suction force through the gap space 94 between the chamber inner wall 53*e* of the piston chamber 53*b* and the peripheral side wall 61*c* of the valve shaft 61*b* is reduced, so that it is possible to prevent unwanted suction through the suction opening 31 of the tip device 16*a*. In FIGS. 11A and 11B, the phantom line indicates the chamber inner wall 53*e* of the piston chamber 53*b*. The solid line indicates the peripheral side wall 61*c* of the valve shaft 61*b*. The gap space 94 between the chamber inner wall 53*e* of the piston chamber 53*b* and the peripheral side wall 61*c* of the valve shaft 61*b* is emphasized for the purpose of clarifying a difference between states with and without the tilt of the piston rod 61.

In the first position, there occurs a moment with which the peripheral groove 73 of the piston rod 61 is pressed to the exhaust port hole 57 by the shoulder projection 86 as the tilting device. There is force of the bias for pressing the peripheral side wall 61*c* of the valve shaft 61*b* having the peripheral groove 73 to the chamber inner wall 53*e* of the piston chamber 53*b* having the exhaust port hole 57. A gap space between the chamber inner wall 53*e* of the piston chamber 53*b* and the peripheral side wall 61*c* of the valve shaft 61*b* is reduced by the bias. It is possible to reduce the suction force through the gap space between the chamber inner wall 53*e* of the piston chamber 53*b* and the peripheral side wall 61*c* of the valve shaft 61*b*, to prevent unwanted suction through the suction opening 31.

In the second position, the lower piston end 61*d* of the piston rod 61 having the end opening 71 comes near to or contacts the end wall 53*d* of the piston chamber 53*b*. Should residual fluid remain between the lower piston end 61*d* of the piston rod 61 and the end wall 53*d* of the piston chamber 53*b*, failure may occur in the return of the piston rod 61 due to an increase in the viscosity of the fluid with time. Such failure is serious typically assuming that the fluid is a contrast agent.

The contrast agent is used for enhancing an image of particular body tissue in a body, such as blood vessels, and for enhancing contrast of the image. Excitation light of a particular wavelength is applied to body tissue together with administration of the contrast agent, for imaging of a fluorescence image. Also, the contrast agent is used for X-ray imaging of the body tissue . A cannula is entered through the suction opening 31 to inject the contrast agent to the body tissue, which is imaged by an apparatus of X-ray fluoroscopy.

Thus, a removal facilitator 90 for facilitating removal of residue is provided in the end opening 71. A tapered inner surface 91 constitutes the removal facilitator 90. A width of the tapered inner surface 91 increases toward the lower piston end 61d. In other words, the diameter of the tapered inner surface 91 decreases from a maximum diameter D1 at the lower piston end 61d to a diameter D2 upwards along the piston rod 61. The maximum diameter D1 of the tapered inner surface 91 is preferably equal to the outer diameter of the peripheral side wall 61c. Note that the maximum diameter D1 of the tapered inner surface 91 can be slightly smaller than the outer diameter of the peripheral side wall 61c.

While the piston rod 61 is in the second position, the tapered inner surface 91 facilitates the suction of residual fluid or contrast agent (contaminant) remaining between the lower piston end 61d of the piston rod 61 and the end wall 53d of the piston chamber 53b. Thus, the contrast agent is removed from the first flow path 72 to the exhaust conduit 33. The tapered inner surface 91 is effective in reducing an area of contact between the lower piston end 61d of the piston rod 61 and the piston chamber 53b. It is possible to prevent stiction of the piston rod 61 to the valve cylinder 53, as the contrast agent remaining between the valve cylinder 53 and the piston rod 61 is minimized.

The operation of the suction button unit 24 in the endoscope apparatus 10 is described now. In case the endoscope system 2 is ready, the camera unit 43 operates for imaging. The air pump 13a and the suction source 14 are set always active for supplying air and suction of fluid. Then the elongated tube 16 is entered in a body cavity, for example, gastrointestinal tract. Light emitted by the light source apparatus 12 is guided through an optical fiber cable within the universal cable 18 and the elongated tube 16 and lighting windows (not shown) of the tip device 16a, and is applied to an object of interest in the body cavity. The camera unit 43 in the tip device 16a outputs an image signal by imaging an object. The image signal is input to the processing apparatus 11 through the cable in the elongated tube 16 and the universal cable 18, so that the monitor display panel 21 is driven to display an image of the image signal.

In case there is no suction from the suction opening 31 during the endoscopic imaging, the button cap 41 in the suction button unit 24 is in the inactive state as illustrated in FIG. 3. The piston rod 61 is in the first position for the closed state. The peripheral groove 73 is aligned with the exhaust port hole 57. However, the side opening 70 is not aligned with the exhaust port hole 57, but closed by the chamber inner wall 53e of the piston chamber 53b. While the piston rod 61 is in the first position, the shoulder projection 86 tilts the piston rod 61 relative to the axis of the valve cylinder 53. Thus, an area of a cross section of the gap space 94 between the valve cylinder 53 and the piston rod 61 can be reduced. The suction force through the suction conduit 32 can be reduced by the amount of the decrease in the area of the cross section between the valve cylinder 53 and the piston rod 61.

While the piston rod 61 is in the first position, the exhaust port hole 57 is set open to the atmosphere by the peripheral groove 73, gap spaces between the flow path surfaces 87-89 and the piston chamber 53b, the space in the support ring 54, the vents 83, the space in the intermediate sleeve 78, and the gap space between the button head 77 and the cover sleeve 79. It is possible to reduce unwanted suction from the suction conduit 32. Also, overload to the suction source 14 can be prevented while there is no suction from the suction opening 31.

In the endoscopic imaging, the button cap 41 is depressed for sucking body fluid or other fluids, to shift the piston rod 61 to the second position for the flow-through state. Upon the start of depressing the button cap 41, the shoulder projection 86 moves away from the cap device 62. The piston rod 61 is released from being tilted relative to the valve cylinder 53 according to the shoulder projection 86. Thus, the piston rod 61 moves smoothly relative to the valve cylinder 53 with high operability.

While the piston rod 61 is in the second position in FIG. 10, the side opening 70 moves and becomes aligned with the exhaust port hole 57. The peripheral groove 73 is opposed to the chamber inner wall 53e of the piston chamber 53b. Thus, the suction port hole 56 communicates with the exhaust port hole 57. Then the exhaust conduit 33, the suction conduit 32 and the tube channel 27 come to communicate with one another with the first flow path 72. Fluid is drawn and removed through the suction opening 31. The fluid is drawn through the tube channel 27, the suction conduit 32, the first flow path 72 and the exhaust conduit 33 and drained to the outside of the endoscope apparatus 10. After the suction of the fluid, force of depressing the button cap 41 is interrupted, to return the piston rod 61 to the first position by the bias of the compression coil spring 63 (bias device).

In the present embodiment, the shoulder projection 86 tilts the piston rod 61 relative to the valve cylinder 53. Suction from the suction conduit 32 to the exhaust port hole 57 can be prevented while the piston rod 61 is in the first position. It is possible to prevent unwanted suction of fluid through the suction opening 31 in an unintended manner while the suction button unit 24 is inactive.

In the above embodiment, the tapered inner surface 91 at the end opening 71 of the piston rod 61 as the removal facilitator 90 can prevent sticking between the piston rod 61 and the valve cylinder 53 in the endoscopy with a contrast agent. Thus, the suction button unit 24 can be pressed for a long time smoothly with high operability.

Figure 12:
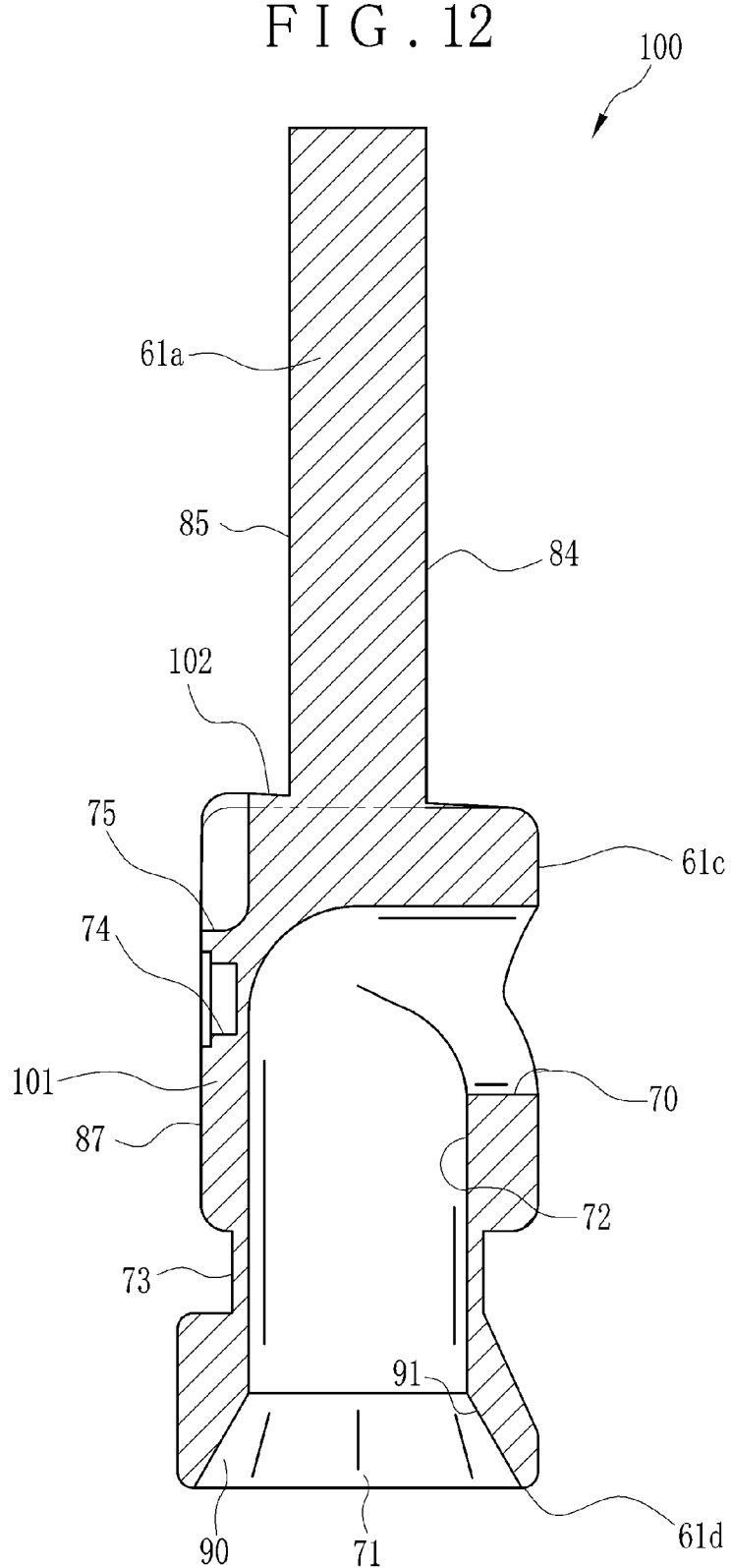
FIG. 12 is a vertical section illustrating another preferred piston rod having an inclined surface for tilting.

In the above embodiment, the shoulder projection 86 of the valve shaft 61b is the tilting device. In FIG. 12, another preferred piston rod 100 or valve stem is illustrated. An inclined surface 102 as a tilting device is formed at one end of a valve shaft 101 or piston shaft to contact the cap device 62. The inclined surface 102 is inclined with reference to a plane perpendicular to the axial direction of the valve shaft 101. Elements of the above embodiment are repeated except for the piston rod 100. The inclined surface 102 is inclined toward the same position as the side opening 70 from a position opposite to the side opening 70 in the radial direction of the piston rod 100. The inclined surface 102 is caused by the compression coil spring 63 to contact the lower end surface 78e of the cap device 62 in a stable manner for the state of the first position. The piston rod 100 becomes tilted with reference to the axis of the valve cylinder 53. Thus, suction from the suction conduit 32 to the exhaust port hole 57 can be prevented while the piston rod 100 is in the first position. Also, the inclined surface 102 is inclined toward the side of the side opening 70 from the opposite side with reference to the axial direction of the piston rod 100. The side opening 70 is pressed tightly on the chamber inner wall 53e of the piston chamber 53b in a biased manner, to prevent unwanted suction.

In the above embodiments, the tilting device is provided in the piston rod 61, 100. However, a tilting device may be provided in the cap device 62, for example, a projection. The projection can project from the lower end surface 78e of the cap device 62, and contact the upper end of the valve shaft 61b of the piston rod for positioning in the first position. The projection is disposed on a side opposite to the side opening 70 in the radial direction, and contacts the valve shaft 61b. Also, an inclined surface as a tilting device may be formed on the cap device 62. The inclined surface can be formed with the lower end surface 78e of the cap device 62, and contact the end of the valve shaft 61b for positioning in the first position. This inclined surface is inclined toward the same position as the side opening from the position opposite to the side opening in the radial direction of the piston rod.

In the above embodiments, the tilting device tilts the piston rod in a tilt direction of the position of the side opening 70 relative to the axis of the valve cylinder 53. However, the tilt direction is not limited. It is possible to tilt the piston rod relative to the axis of the cylinder in the closed state of the button unit.

Figure 13:
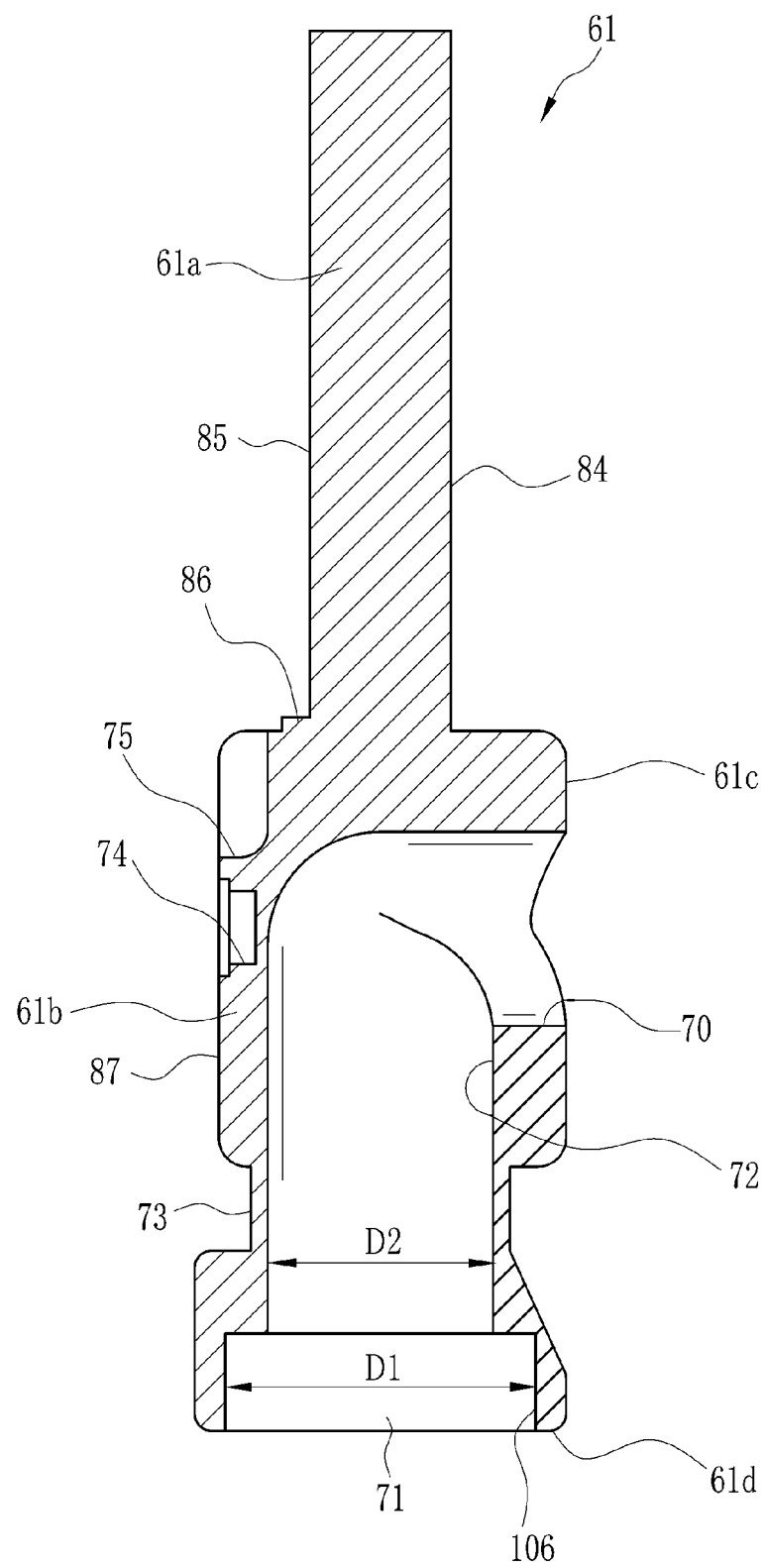
FIG. 13 is a vertical section illustrating one preferred piston rod with an inner shoulder at a lower end.

In the above embodiments, the tapered inner surface 91 for the removal facilitator 90 is formed with the end opening 71 of the piston rod 61. In FIG. 13, another preferred embodiment is illustrated, in which an inner shoulder 106 is formed with the piston rod 61 with a larger diameter than the first flow path 72 in the end opening 71. It is possible to reduce residual contrast agent present from between the valve cylinder 53 and the piston rod 61, to prevent sticking of the piston rod 61 on the valve cylinder 53.

Figure 14:
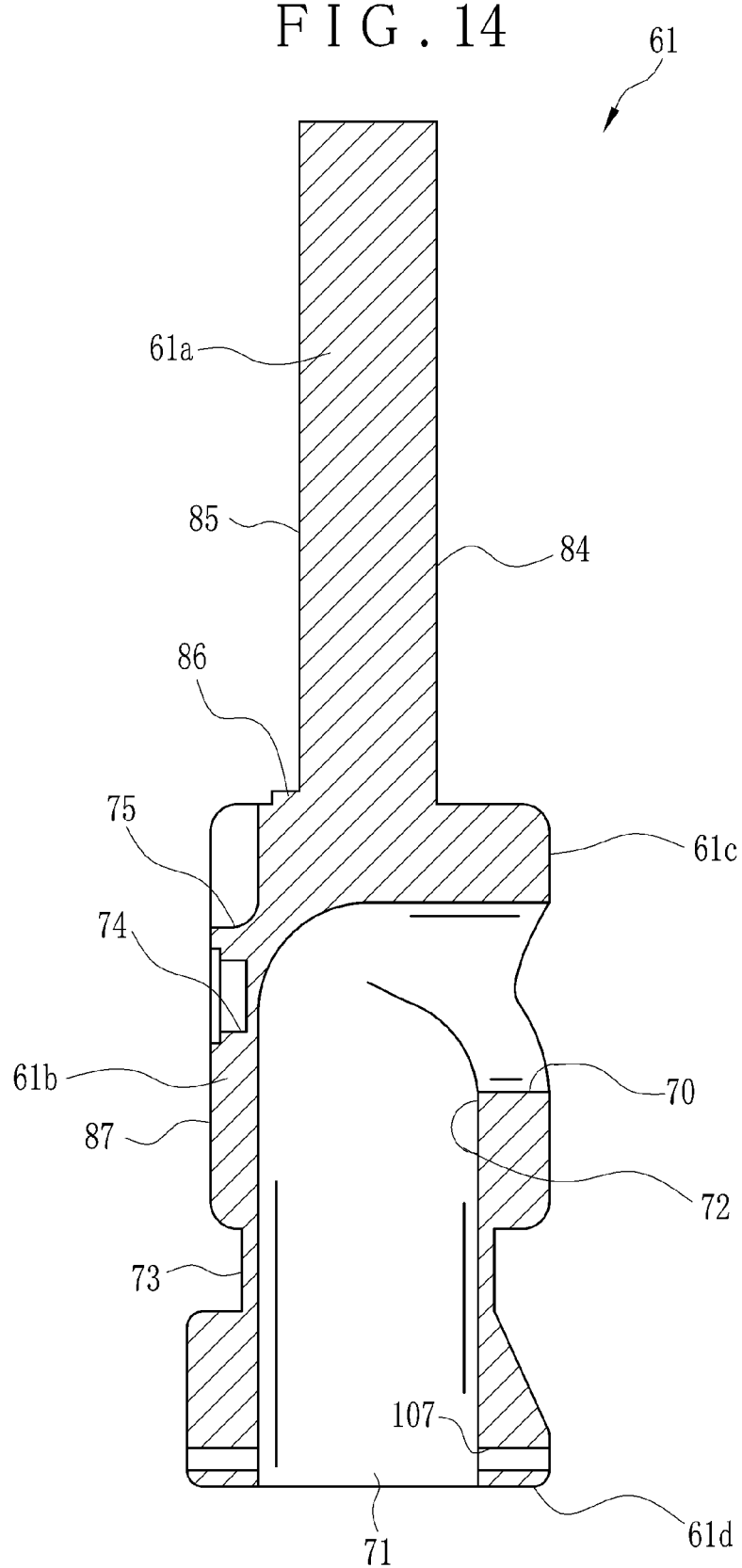
FIG. 14 is a vertical section illustrating still another preferred piston rod having a discharge hole at a lower end.

In FIG. 14, still another preferred embodiment is illustrated. Removal facilitating discharge holes 107 for facilitating removal of residue are formed in the piston rod 61 near to the suction port hole 56 and come through the peripheral side wall 61c from the first flow path 72. Should a contrast agent from the suction conduit 32 enter the piston chamber 53b, the contrast agent is discharged through the discharge holes 107 in the peripheral side wall 61c. It is possible to prevent sticking of the contrast agent between the valve cylinder 53 and the piston rod 61. Furthermore, it is possible to combine two or more examples of a removal facilitating structure for discharging residual fluid. For example, a tapered inner surface or an inner shoulder can be formed with the end opening 71 in combination with the discharge holes 107.

In the above embodiment, the endoscope apparatus 10 is a type having the CCD image sensor. However, the endoscope apparatus 10 of the invention can be a type in which an optical image guide device is used for transmitting image light.

Also, materials for the piston rod 61 can be metal, resin or other compounds. The flow path structure of the piston rod 61 is not limited to the above-described example having the flow path surface 87 and the like. The feature of the invention can be used with a suction button unit or switching valve unit having other flow path structures.

In the above embodiment, the suction button unit or switching valve unit is used for the endoscope apparatus. However, a switching valve unit of the invention can be used for a probe, catheter, or other apparatuses having conduits, for medical use or for diagnosis.

EXAMPLES

Examples of the invention are hereinafter described. The invention is not limited to those examples.

In Example 1, the suction button unit 24 according to the first embodiment had the piston rod 61 of which the valve shaft 61b had the outer diameter of 6.6 mm. A dimensional tolerance in relation to the outer diameter of the valve shaft 61b was equal to or more than −0.012 mm and equal to or less than −0.004 mm.

A height of protrusion of the shoulder projection 86 was 0.24 mm. A dimensional tolerance in relation to the height of protrusion of the shoulder projection 86 was equal to or more than −0.03 mm and equal to or less than 0.05 mm. The valve cylinder 53 had the piston chamber 53b with the inner diameter of 6.6 mm. A dimensional tolerance in relation to the inner diameter of the piston chamber 53b was equal to or more than -0 mm and equal to or less than +0.009 mm. A fit tolerance of the valve cylinder 53 was H6. A clearance space (gap space 94) between the piston rod 61 and the valve cylinder 53 was equal to or more than 4 µm and equal to or less than 21 µm.

In Comparison 1, Example 1 was repeated but with a difference in that the piston rod did not have the shoulder projection 86. The other parts, sizes, dimensional tolerance, fit tolerance and clearance were equal to those of Example 1.

Samples of the suction button unit 24 of Example 1 and Comparison 1 were used to measure pressure of the suction of the suction conduit 32 in the closed state for three measurement sessions. For the experiment, the pressure of the suction of the suction source 14 was 40 kPa. A result obtained from the measurement was indicated in Table 1.

TABLE 1

|  |  | Pressure (kPa) of the suction in the closed state |
|---|---|---|
| Example 1 | First measurement session | 3.2 |
|  | Second measurement session | 3.2 |
|  | Third measurement session | 3.1 |
| Comparison 1 | First measurement session | 7.0 |
|  | Second measurement session | 6.8 |
|  | Third measurement session | 7.2 |

According to the results of Example 1 and Comparison 1, it was found that the suction pressure in the closed state was lower in Example 1 than in Comparison 1. It was concluded that the suction force from the suction conduit 32 to the exhaust port hole 57 was decreased.

Also, Example 2 was prepared, and the use of the suction button unit 24 of Example 1 was repeated. In addition, a contrast agent was drawn by suction through the suction opening according to a predetermined condition to be described later, to test operability of the suction button unit 24.

In Comparison 2, Example 2 was repeated but with a difference in that the first flow path 72 had an inner surface with a constantly equal diameter D2 to the lower piston end without the tapered form at the end opening 71. A contrast agent was drawn by suction through the suction conduit 32 in the same predetermined condition as Example 2, to test operability of the suction button unit 24.

The predetermined condition of the test was as follows. At first, the suction button unit 24 was depressed and kept for the flow-through state for one (1) second. Then the suction button unit 24 was released and made inactive. Those steps of the depression and release were repeated cyclically. A first availability time period and a second availability time period were measured for three measurement sessions in combination of the suction button unit 24 with the contrast agent. Results of the measurement were indicated in Table 2. As conditions of the measurement, pressure of the suction of the suction apparatus was kPa. The contrast agent was CON-RAY 60% (trade name) manufactured by Daiichi Sankyo Co. Ltd.

The first availability time period was a period of a start of the sticking, and was a period of a situation in which a return to the first position after releasing the piston rod was within a duration less than 3 seconds. The first availability time period was utilized as information of a start of sticking of the piston rod 61 to the piston chamber 53b with the contrast agent and weighted slide of the piston rod 61. The second availability time period was a period of completion of the sticking, and was a period of a situation in which a return to the first position after releasing the piston rod was made upon a lapse of 3 seconds or more. The second availability time period was utilized as information of impossibility of smooth slide of the piston rod 61.

TABLE 2

|  |  | First availability time period before sticking | Second availability time period before sticking |
|---|---|---|---|
| Example 2 | First measurement session | 11 min. | 31 min. |
|  | Second measurement session | 7 min. | 13 min. |
|  | Third measurement session | 14 min. | 20 min. |
| Comparison 2 | First measurement session | 2 min. 20 sec. | 6 min. |
|  | Second measurement session | 3 min. | 7 min. |
|  | Third measurement session | 3 min. | 8 min. |

According to those results, the first and second availability time periods were longer in Example 2 than in Comparison 2. In conclusion, it was possible in Example 2 to prevent sticking between the piston rod 61 and the valve cylinder 53.

Consequently, it is possible to reduce residual contrast agent present between the piston rod and the piston chamber by use of the removal facilitating structure formed in the end opening in the piston rod, to prevent sticking between the piston rod and the valve cylinder.

According to a preferred embodiment of the present invention, a switching valve unit for changeover between a suction source and a suction opening includes a piston chamber extending axially. A suction port hole is formed at a lower end of the piston chamber, for connection with the suction opening. An exhaust port hole is formed in a chamber inner wall of the piston chamber, for connection with the suction source. A piston rod is received in the piston chamber, has a first piston end protruding upwards, for shifting from a first position to a second position upon depression. A flow path structure externally opens the exhaust port hole in case the piston rod is in the first position, and causes the exhaust port hole to communicate with the suction port hole in case the piston rod is in the second position. A tilting device tilts the piston rod relative to an axial direction of the piston chamber while the piston rod is in the first position.

According to another preferred embodiment of the present invention, a switching valve unit for changeover between a suction source and a suction opening includes a piston chamber extending axially. A suction port hole is formed at a lower end of the piston chamber, for connection with the suction opening. An exhaust port hole is formed in a chamber inner wall of the piston chamber, for connection with the suction source. A piston rod is received in the piston chamber, has a first piston end protruding upwards, for shifting from a first position to a second position upon depression. A flow path structure externally opens the exhaust port hole in case the piston rod is in the first position, and causes the exhaust port hole to communicate with the suction port hole in case the piston rod is in the second position. A tilting device tilts the piston rod relative to an axial direction of the piston chamber while the piston rod is in the first position. An end opening is formed in the piston rod, for constituting the flow path structure, and communicating with the suction port hole. A removal facilitator is disposed at the end opening, for facilitating suction of residue remaining in the end opening.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A switching valve unit for an endoscope apparatus, for changeover in a conduit extending between a suction source and a suction opening, comprising:
    a valve cylinder, mounted on a control handle of said endoscope apparatus, having a piston chamber;
    a cylinder opening formed at an upper end of said piston chamber;
    a suction port hole, formed at a lower end of said piston chamber, and adapted to connection with said suction opening;
    an exhaust port hole, formed in a chamber inner wall of said piston chamber, and adapted to connection with said suction source;
    a piston rod, received in said piston chamber, having a first piston end protruding from said cylinder opening, for shifting from a first position to a second position upon depression;
    a side opening, formed in a peripheral side wall of said piston rod, closed by said chamber inner wall of said piston chamber in case said piston rod is in said first position, and aligned with said exhaust port hole in case said piston rod is in said second position;
    an end opening, formed at a second piston end of said piston rod, for alignment with said suction port hole;
    a first flow path, formed in said piston rod between said side opening and said end opening, for communication of said exhaust port hole to said suction port hole in case said piston rod is in said second position;
    a peripheral groove, formed in said peripheral side wall of said piston rod, aligned with said exhaust port hole in case said piston rod is in said first position, and closed by said chamber inner wall of said piston chamber in case said piston rod is in said second position;

a flow path surface formed with said peripheral side wall of said piston rod to extend from said peripheral groove to said first piston end of said piston rod;

a second flow path, constituted by said peripheral groove and said flow path surface, for externally opening said exhaust port hole in case said piston rod is in said first position;

an anti-rotation device for preventing said piston rod from rotating relative to said piston chamber;

a tilting device for tilting said piston rod relative to an axial direction of said valve cylinder while said piston rod is in said first position.

2. A switching valve unit as defined in claim 1, further comprising:

a cap device, disposed on said valve cylinder, for keeping said piston rod positioned in said cylinder opening of said piston chamber;

a button cap mounted on said first piston end;

a bias device, disposed between said button cap and said cap device, for biasing said piston rod to said first position, to press said piston rod to said cap device;

wherein said button cap moves said piston rod to said second position and contacts said cap device upon being depressed against said bias device.

3. A switching valve unit as defined in claim 2, wherein said tilting device includes a projection, formed with a first part selected from said piston rod and said cap device, to protrude toward a second part selected from said piston rod and said cap device, for contacting said second part in case said piston rod is in said first position.

4. A switching valve unit as defined in claim 2, wherein said tilting device includes an inclined surface, formed with a first part selected from said piston rod and said cap device, for contacting a second part selected from said piston rod and said cap device in case said piston rod is in said first position.

5. A switching valve unit as defined in claim 2, wherein said cap device supports said piston rod and said bias device, and is removable from said valve cylinder.

6. A switching valve unit as defined in claim 1, wherein said tilting device tilts said piston rod in a direction toward said side opening relative to said valve cylinder, for tightening closing of said side opening with said chamber inner wall.

7. A switching valve unit as defined in claim 1, further comprising a removal facilitator, disposed at said end opening, for facilitating suction of residue remaining in said end opening.

8. A switching valve unit as defined in claim 7, wherein said removal facilitator includes a tapered surface, formed in said end opening, and inclined for increasing a diameter toward said second piston end.

9. A switching valve unit as defined in claim 7, wherein said removal facilitator is an inner shoulder at which an inner diameter of said end opening is larger than an inner diameter of said first flow path.

10. A switching valve unit as defined in claim 7, wherein said removal facilitator includes a discharge hole, disposed near to said end opening, and formed through said peripheral side wall of said piston rod from said first flow path.

11. An endoscope apparatus comprising:

an elongated tube for entry in a body cavity;

a control handle disposed at a proximal end of said elongated tube;

an exhaust conduit, disposed to extend from said control handle, for connection to a suction source;

a suction conduit, formed through said elongated tube, having a suction opening at a distal end thereof;

a valve cylinder, mounted on said control handle, having a piston chamber;

a cylinder opening formed at an upper end of said piston chamber;

a suction port hole, formed at a lower end of said piston chamber, and coupled with said suction conduit;

an exhaust port hole, formed in a chamber inner wall of said piston chamber, and coupled with said exhaust conduit;

a piston rod, received in said piston chamber, having a first piston end protruding from said cylinder opening, for shifting from a first position to a second position upon depression;

a side opening, formed in a peripheral side wall of said piston rod, closed by said chamber inner wall of said piston chamber in case said piston rod is in said first position, and aligned with said exhaust port hole in case said piston rod is in said second position;

an end opening, formed at a second piston end of said piston rod, for alignment with said suction port hole;

a first flow path, formed in said piston rod between said side opening and said end opening, for communication of said exhaust port hole to said suction port hole in case said piston rod is in said second position;

a peripheral groove, formed in said peripheral side wall of said piston rod, aligned with said exhaust port hole in case said piston rod is in said first position, and closed by said chamber inner wall of said piston chamber in case said piston rod is in said second position;

a flow path surface formed with said peripheral side wall of said piston rod to extend from said peripheral groove to said first piston end of said piston rod;

a second flow path, constituted by said peripheral groove and said flow path surface, for externally opening said exhaust port hole in case said piston rod is in said first position;

an anti-rotation device for preventing said piston rod from rotating relative to said piston chamber;

a tilting device for tilting said piston rod relative to an axial direction of said valve cylinder while said piston rod is in said first position.

* * * * *